(12) United States Patent
Alexandersson

(10) Patent No.: US 9,757,519 B2
(45) Date of Patent: *Sep. 12, 2017

(54) MEDICAMENT DELIVERY DEVICE

(71) Applicant: SHL Group AB, Nacka Strand (SE)

(72) Inventor: Oscar Alexandersson, Haninge (SE)

(73) Assignee: SHL Group AB, Nacka Strand (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/993,721

(22) Filed: Jan. 12, 2016

(65) Prior Publication Data

US 2016/0121048 A1  May 5, 2016

Related U.S. Application Data

(63) Continuation of application No. 14/747,869, filed on Jun. 23, 2015, which is a continuation of application
(Continued)

(30) Foreign Application Priority Data

Oct. 30, 2009 (SE) .................... 0950807-8

(51) Int. Cl.
*A61M 5/31* (2006.01)
*A61M 5/20* (2006.01)
(Continued)

(52) U.S. Cl.
CPC ............ *A61M 5/20* (2013.01); *A61M 5/2033* (2013.01); *A61M 5/3202* (2013.01);
(Continued)

(58) Field of Classification Search
CPC .... A61M 2005/2013; A61M 2005/206; A61M 2205/581; A61M 2205/582;
(Continued)

(56) References Cited

U.S. PATENT DOCUMENTS 5,137,516 A * 8/1992 Rand ........................ A61J 1/00
604/136
6,221,046 B1   4/2001 Burroughs et al.
(Continued)

FOREIGN PATENT DOCUMENTS

EP   1345950 B1   5/2006
WO   0247746 A1   6/2002
(Continued)

*Primary Examiner* — Gerald Landry, II
(74) *Attorney, Agent, or Firm* — McDonnell Boehnen Hulbert & Berghoff LLP

(57) ABSTRACT

A medicament delivery device includes a generally elongated tubular housing having opposite proximal and distal parts; a needle shield sleeve slidably and coaxially arranged inside the housing with a proximal part of the sleeve protruding a distance outside the proximal part of the housing; a syringe carrier mechanism having a syringe carrier slidably and coaxially arranged within the needle shield sleeve, a syringe having a stopper, a medicament, and a needle, the syringe being coaxially arranged within the syringe carrier; and a holding member connected to the syringe carrier; a first activator member an a second activator member; a drive mechanism adapted to accumulate a drive force for moving the syringe carrier mechanism in a first step and a second step. The second activator member is arranged within an information device for producing audible, visual, and/or tactile feedback to a user about a completed injection.

20 Claims, 6 Drawing Sheets

Related U.S. Application Data

No. 13/858,692, filed on Apr. 8, 2013, now Pat. No. 9,302,047, which is a continuation of application No. 13/500,913, filed as application No. PCT/SE2010/051004 on Sep. 20, 2010, now Pat. No. 8,414,533.

(60) Provisional application No. 61/249,675, filed on Oct. 8, 2009.

(51) Int. Cl.
  *A61M 5/32* (2006.01)
  *A61M 5/315* (2006.01)

(52) U.S. Cl.
  CPC ............ *A61M 5/326* (2013.01); *A61M 5/3157* (2013.01); *A61M 2005/206* (2013.01); *A61M 2005/2013* (2013.01); *A61M 2005/2026* (2013.01); *A61M 2205/581* (2013.01); *A61M 2205/582* (2013.01); *A61M 2205/583* (2013.01); *A61M 2205/584* (2013.01)

(58) Field of Classification Search
  CPC ...... A61M 2205/583; A61M 2205/584; A61M 5/3157; A61M 5/2033; A61M 5/326
  USPC ........ 604/131, 135, 136, 192, 197, 198, 210
  See application file for complete search history.

(56) References Cited

U.S. PATENT DOCUMENTS

| | | | | |
|---|---|---|---|---|
| 6,371,939 B2* | 4/2002 | Bergens | ............. | A61M 5/2033 604/156 |
| 2004/0097883 A1 | 5/2004 | Roe | | |
| 2005/0277886 A1* | 12/2005 | Hommann | .......... | A61M 5/2033 604/136 |
| 2007/0021720 A1* | 1/2007 | Guillermo | .......... | A61M 5/2033 604/187 |
| 2007/0265568 A1 | 11/2007 | Tsals et al. | | |
| 2008/0154200 A1* | 6/2008 | Lesch | ................ | A61M 5/2033 604/135 |
| 2009/0012479 A1* | 1/2009 | Moller | ................ | A61M 5/3155 604/211 |
| 2009/0312705 A1 | 12/2009 | Grunhut et al. | | |
| 2009/0318864 A1* | 12/2009 | Carrel | .................. | A61M 5/326 604/117 |
| 2010/0063444 A1 | 3/2010 | Wikner | | |
| 2010/0094214 A1 | 4/2010 | Abry et al. | | |
| 2010/0152659 A1* | 6/2010 | Streit | ................ | A61M 5/2033 604/136 |
| 2010/0152671 A1* | 6/2010 | Raab | ................ | A61M 5/31551 604/207 |
| 2010/0152672 A1* | 6/2010 | Raab | ................ | A61M 5/31555 604/208 |
| 2010/0249705 A1* | 9/2010 | Kronestedt | ......... | A61M 5/2033 604/134 |
| 2010/0249721 A1* | 9/2010 | Guillermo | .......... | A61M 5/2033 604/246 |
| 2011/0077599 A1* | 3/2011 | Wozencroft | ........ | A61M 5/2033 604/192 |
| 2011/0245770 A1* | 10/2011 | Carrel | .................. | A61M 5/326 604/117 |
| 2012/0010575 A1 | 1/2012 | Jones et al. | | |

FOREIGN PATENT DOCUMENTS

| | | |
|---|---|---|
| WO | 2004028598 A1 | 4/2004 |
| WO | 2007132535 A2 | 11/2007 |

* cited by examiner

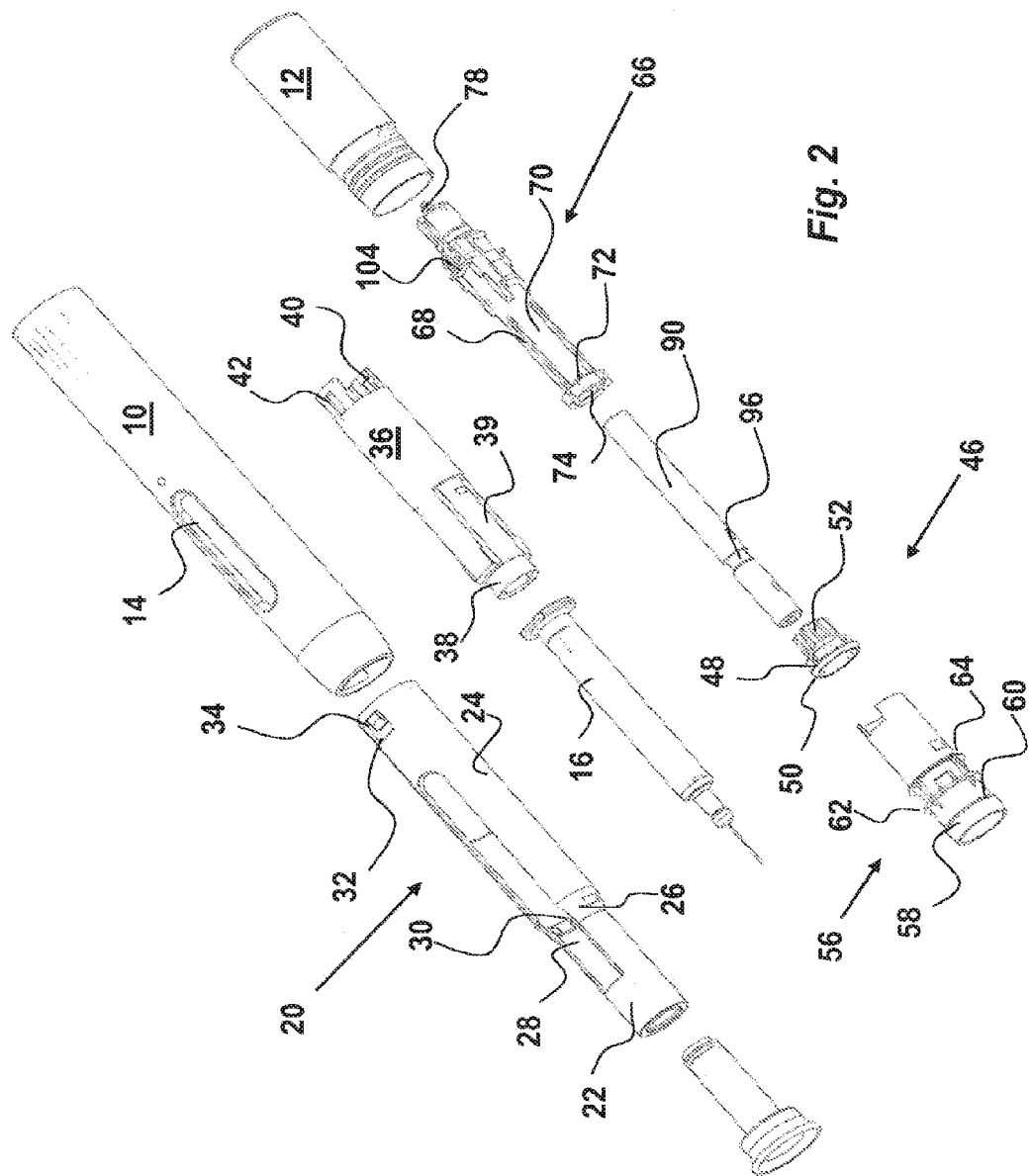

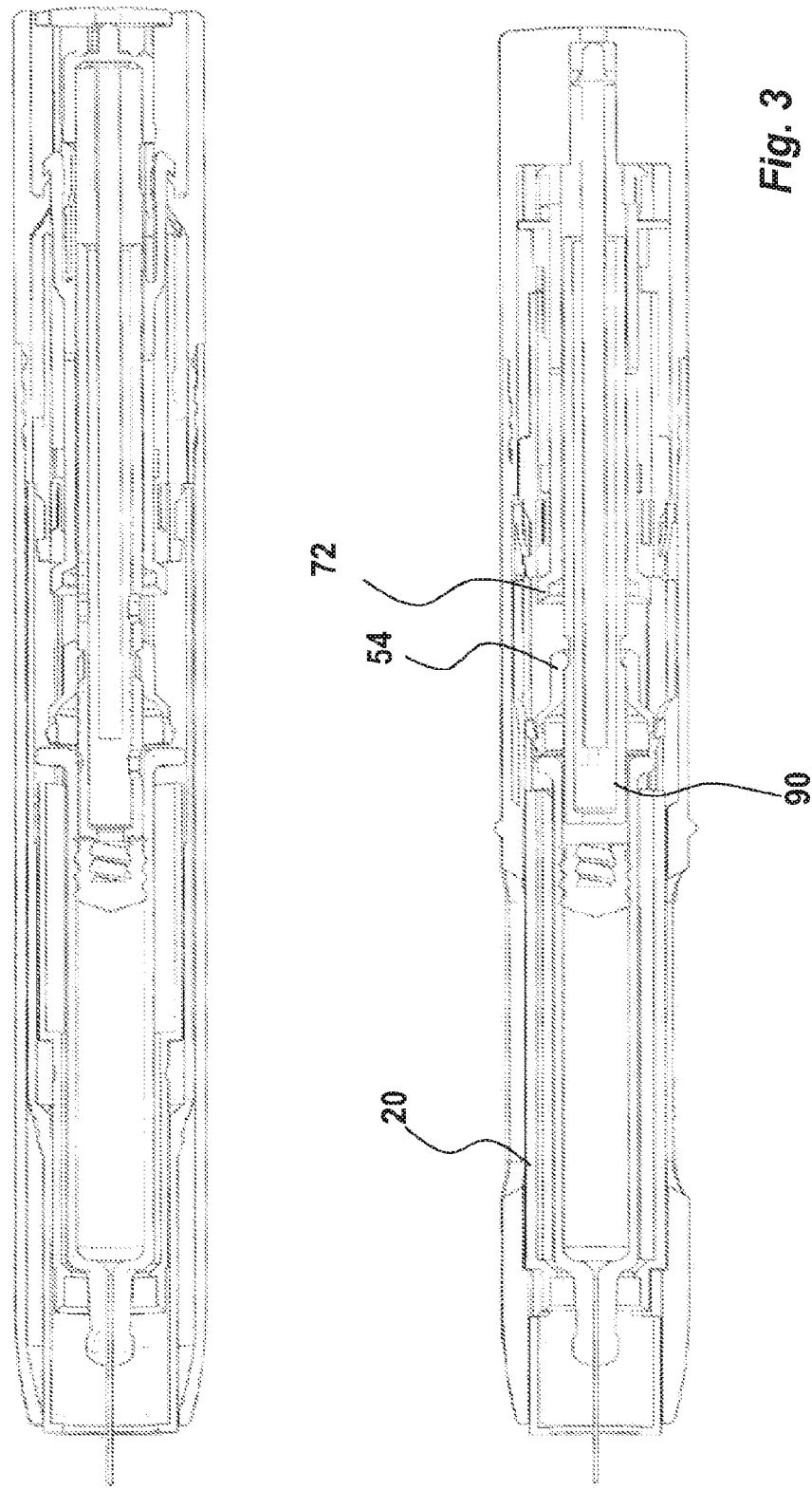

MEDICAMENT DELIVERY DEVICE

CROSS REFERENCE TO RELATED APPLICATIONS

The present application is a continuation application of U.S. patent application Ser. No. 14/747,869 filed Jun. 23, 2015, which is a continuation application of U.S. patent application Ser. No. 13/858,692, filed Apr. 8, 2013, which is a continuation of U.S. patent application Ser. No. 13/500,913, filed Apr. 8, 2012, which is a 371 of International Patent Application No. PCT/SE2010/051004, filed Sep. 20, 2010 which claims the benefit of U.S. Provisional Patent Application No. 61/249,675, filed Oct. 8, 2009 and Swedish Patent Application No 0950807-8, filed Oct. 30, 2009 the entire contents of which are incorporated entirely herein by reference.

TECHNICAL AREA

The present invention relates to a medicament delivery device and in particular a device which is capable of providing information regarding a completed medicament delivery step.

BACKGROUND OF INVENTION

There are a number of devices on the market that are capable of automatically or semi-automatically delivering doses of medicament, where these devices comprise a number of inter-acting components for obtaining the desired functions.

One type of such delivery devices is an injector capable of delivering doses of medicament, having functions such as penetration of the patient's skin and a subsequent injection of medicament. One such device is for example disclosed in the document EP 1349590, comprising an activation mechanism in the form of a button placed at its distal end. The button may only activate the mechanism if the front end of the device is pressed against an injection site. When done so and the button is pressed, the penetration mechanism inside the injector is released whereby the needle is pushed into the body of the patient. After this, the injection is performed.

When the injection is completed, the patient withdraws the injector with the needle from the injection site, whereby a needle shield is pushed forward until it surrounds the needle and is then locked.

With an injector of the above described type there is often a desire for the user to know when the injection is completed and it is safe to remove the injector. A few solutions of informing the user of the status of the injection have been developed.

U.S. Pat. No. 6,221,046 describes an injection device having an "end of injection click: including an extension of a flexible tab of a dose dial mechanism. The tab with the extension falls into a groove in the housing, causing an audible click at the end of injection. US 2004/0097883 discloses a similar end of injection click solution.

However, even if some solutions have been presented regarding informing a user of a medical delivery device, there is still room for improvements, especially regarding the delivering step of a medical delivery device.

BRIEF DESCRIPTION OF INVENTION

The aim of the present invention is to remedy the drawbacks of the state of the art devices.

This aim is solved according to the present invention by a medicament delivery device according to the features of the independent patent claim.

Preferable embodiments form the subject of the dependent patent claims.

According to a main aspect of the invention it is characterised by a medicament delivery device comprising a generally elongated tubular housing having opposite proximal and distal parts; a needle shield sleeve slidably and coaxially arranged inside the housing and wherein a proximal part of said sleeve protrudes a distance outside the proximal part of the housing; a syringe carrier mechanism comprising a syringe carrier slidably and coaxially arranged within the needle shield sleeve, a syringe comprising a stopper, a medicament and a needle, wherein said syringe is coaxially arranged within said syringe carrier, and a holding member connected to the syringe carrier; a first activator member slidably and coaxially arranged within the housing and connected to said needle shield sleeve; a second activator member slidably and coaxially arranged within the first activator member; a drive mechanism slidably and coaxially arranged within the second activator member and releasibly connected to the holding member and to the second activator member, wherein said drive mechanism is adapted to accumulate a drive force for moving said syringe carrier mechanism in a first step for penetrating the needle into an injection site and to move said stopper in a second step for expelling the medicament through the needle, and wherein said drive mechanism is controlled by the first and the second activator members; wherein said second activator member is arranged with information means arranged to cooperate with corresponding interacting means arranged on the distal part of the elongated tubular housing after the medicament is completely expelled such that a remaining drive force of the accumulated drive force in the drive mechanism forces the second activator member to be displaced towards the distal part of the elongated tubular housing for producing audible, visual and/or tactile feedback to a user about a completed injection.

According to another aspect of the invention, said information means comprises an information member attached to a distal transversal end wall of the second activator member, and said corresponding interacting means comprises an opening arranged on a distal wall of the distal part of the elongated tubular housing.

According to a further aspect of the invention, said information member is provided with a characteristic colour.

According to yet another aspect of the invention, the drive mechanism comprises a plunger rod arranged to act on the stopper inside said syringe, and a pre-tensioned first compression spring having a force capable of urging said plunger rod to move in a first step said syringe carrier mechanism for penetrating the needle into an injection site and in a second step said stopper for expelling the medicament through the needle.

According to another aspect of the invention, the plunger rod is slidably and coaxially arranged within the second activator member and the pre-tensioned first compression spring is coaxially arranged within the plunger rod between a proximal end wall of the plunger rod and the distal transversal end wall of the second activator member.

According to a further aspect of the invention, the second activator member comprises flexible tongues having annular inwardly directed ledges, wherein the holding member comprises flexible tongues having annular inwardly directed ledges, and wherein the plunger rod comprises a circumferential groove having a mutual shape as that of the ledges of the second activator member and as that of the ledges of the holding member so that the annular inwardly directed ledges of the second activator member and the radial inwardly directed ledges of the holding member fit into the groove.

According to yet another aspect of the invention, the plunger rod arranged to be held against the force of the pre-tensioned first compression spring by the inwardly directed ledges of the tongues of the second activator member situated in the groove of the plunger rod, and by the first activator member which surrounds and prevents the tongues from moving radially outwards.

According to another aspect of the invention, the device further comprises a pre-tensioned second compression spring having an annular proximal end resting on a second annular ring of the first activator member and an annular distal end resting on the proximal surface of stop ledges of the second activator member.

According to a further aspect of the invention, the needle shield sleeve and the first activator member connected to it are arranged to be moved coaxially and distally in relation to the housing and to the second activator member when the proximal part of said needle shield sleeve is pressed against the injection site for allowing the inwardly directed ledges of the tongues of the second activator member to be released from the groove of the plunger rod, such that the force form the pre-tensioned first compression spring urges said plunger rod to move in a first step said syringe carrier mechanism and in a second step said stopper.

According to yet another aspect of the invention, the second activator member is arranged to be coaxially and distally moved by a remaining force of the pre-tensioned first compression spring after the distal end of the plunger rod pass the ledges of the second activator member such that the tongues are radially moved inwards, whereby the distal transversal end wall of the second activator member strikes against a distal wall of the distal housing part giving an audible signal indicating that the injection has been completed and that the device can be safely removed from the injection site.

According to another aspect of the invention, said information member protrudes trough said opening becoming tactile and/or visible to provide tactile and/or visual information indicating that the injection has been completed and that the device can be safely removed from the injection site when the second activator member is coaxially and distally moved.

According to a further aspect of the invention, the needle shield sleeve and the first activator member are arranged to be coaxially and proximally moved in relation to the housing and to the second activator member by a force from the pre-tensioned second compression spring acting on the first activator member and thus on the needle shield connected to it for covering the needle, when the proximal part of the needle shield sleeve is removed from the delivery site.

According to yet an aspect of the invention, the first activator member comprises ribs on its inner surface arranged to interact with a band-shaped part of the second activator member after the needle shield sleeve and the first activator member are coaxially and proximally moved, for preventing any attempts to push the needle shield sleeve distally into the device.

There are a number of advantages with the present invention. Because the user is provided with information regarding the completed injection, he/she can safely remove, the medicament delivery device from the delivery site, knowing that the injection is completed.

An advantage is that the remaining force of the compression spring means used for penetration and injection is used for providing the information to the user.

In this aspect the information could be visual, i.e. that the user can actually see that the injection has been performed through an opening in the device, like a window or a passage. Further in order to enhance the visibility the indicator could have a bright and/or different colour than the rest of the device.

Further the information member could also be made to protrude through the housing of the device, thereby also providing tactile information to the user as well as visible.

In addition to the visual and/or tactile information the device according to the invention could be audible in that there is a distinct sound when the injection has been performed.

A preferable arrangement of the information member is arranged at the distal end of the device, which facilitates the design since it does not require any more components than the second activator member in order to provide an information function.

In all several ways of positively indicating the performed injection is obtained with the present invention.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIGS. 1a, b show cross-sectional side views of a medicament delivery device according to the present invention, where FIG. 1b is taken 90° in relation to FIG. 1a;

FIG. 2 is an exploded view of the medicament delivery device of FIG. 1, and

FIGS. 3-6 are cross-sectional side views of the medicament delivery device according to the present invention in different functional states.

DETAILED DESCRIPTION OF THE INVENTION

In the present application, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

Figure 1A:
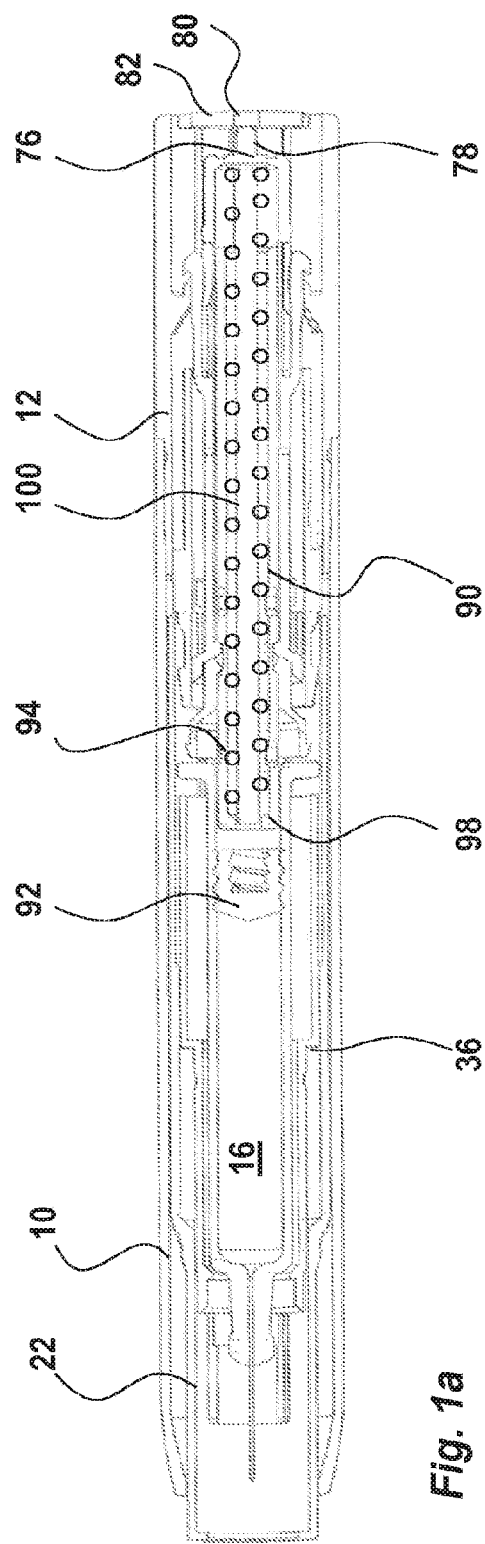
Figure 1B:
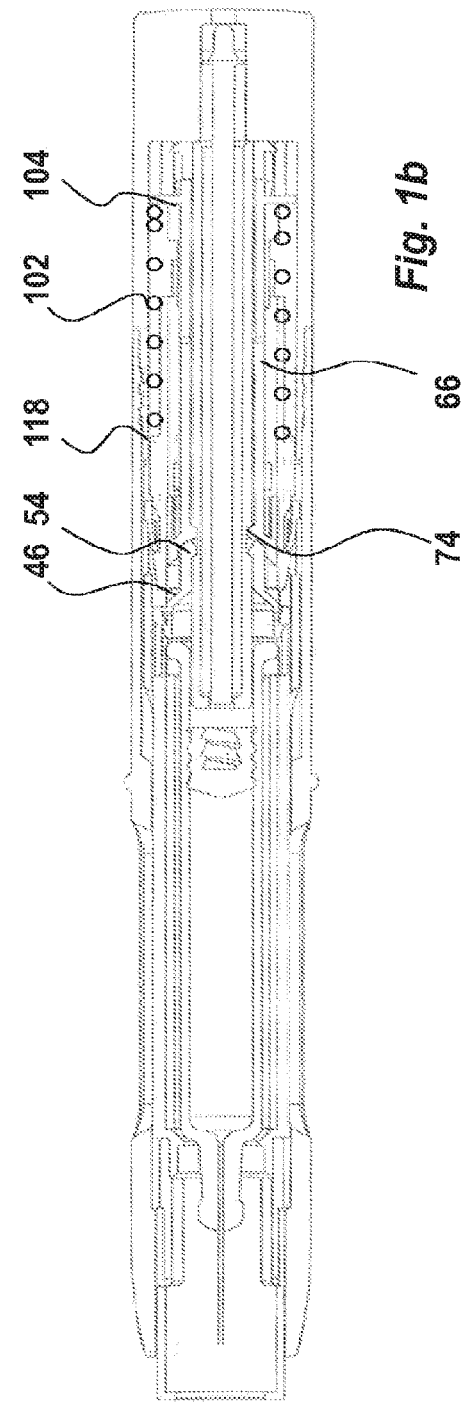

The medicament delivery device, e.g. an auto-injector as seen in FIG. 1, comprises a generally elongated tubular housing having opposite proximal 10 and distal 12 parts. The proximal housing part 10 is arranged with elongated openings 14 for viewing a syringe 16 which contains a liquid medicament, FIG. 2. The distal part is arranged with engagement means as annular recesses e.g. on its inner surface adapted to interface with corresponding engagement means on e.g. the proximal outer surface of the proximal part.

The device further comprises a needle shield sleeve 20, FIG. 2, hereinafter named needle shield, wherein said needle shield comprises a proximal part 22 having a certain diameter and a distal part 24 having a diameter larger than the proximal part, where these parts are joined by an intermediate conical part 26, FIG. 2. Two elongated grooves 28 are arranged along the needle shield, on opposite sides of the needle shield, also for viewing the syringe 16, FIG. 2. On the inner surface of the conical part 26, a circumferential ledge 30 is arranged, FIG. 2. At the distal end of the needle shield two openings 32 are arranged opposite each other, where each opening is arranged with a somewhat inwardly projecting, flexible, tongue 34, FIG. 2. The needle shield sleeve 20 is slidably and coaxially arranged inside the housing and the proximal part of said sleeve protrudes a distance outside the proximal part of the housing.

The device also comprises a syringe carrier mechanism comprising a syringe carrier 36 slidably and coaxially arranged within the needle shield sleeve; the syringe 16 comprising a stopper 92, the medicament and a needle, wherein said syringe is coaxially arranged within said syringe carrier; and a holding member 46 connected to the syringe carrier.

The syringe carrier 36 has the form of a general tubular body and the proximal part of the syringe carrier is arranged with a neck portion 38 of lesser diameter, FIG. 2 Adjacent the neck portion cut-outs have been made on either side to form guide surfaces 39. These surfaces cooperate with corresponding shapes of the inner surface of the needle shield in order to obtain a stop mechanism against rotation of the syringe carrier relative the needle shield. The distal end of the syringe carrier is arranged with two distally extending tongues 40, where each tongue is arranged with an opening 42 and an inwardly directed ledge on the distal edge of each opening, FIG. 2. The syringe carrier is further arranged with radial inwardly directed flanges on its inner surface in order to obtain a space between the syringe carrier wall and the syringe 16 to be placed inside.

The holding member 46, FIG. 2, comprises a ring-shaped body 48 having an annular ledge 50 arranged around its circumference and a number of flexible tongues 52 directed towards the distal end of the device and wherein each tongue 52 is arranged with radial inwardly directed ledges 54, FIG. 1 *b*.

The device also comprises a first activator member 56 which is slidably and coaxially arranged within the housing and connected to the needle shield sleeve 20 as will be described below, which has a tubular shape and which comprises a proximal end with a conical part 58 ending in a ledge 60 on its outer surface, FIG. 2. At a distance from the ledge 60, a first annular ring 62 is arranged on the outer surface, FIG. 2. A second annular ring 64 is also arranged a further distance from the ledge 60.

The device further comprises a second activator member 66 which is slidaby and coaxially arranged within the first activator member 56 and which has a mainly tubular shape. A number of longitudinally directed cut-outs 68 are arranged along the proximal outer surface of the second activator member so as to form flexible tongues 70, FIG. 2. The proximal end of each flexible tongue 70 has an inclined transition surface which meets with a band-shaped part 72 with enlarged diameter, FIG. 3. On the inner surface adjacent the transition surface, an annular inwardly directed ledge 74 is arranged, FIG. 1 *b*. Further, the second activator member 66 is arranged with information means arranged to cooperate with corresponding interacting means arranged on the distal part of the elongated tubular housing. Said information means comprises an information member 78 attached to a distal transversal end wall 76 of the second activator member, and said corresponding interacting means comprises an opening 80 arranged on a distal wall 82 of the distal part of the elongated tubular housing, FIG. 1*a*.

The device also comprises a drive mechanism which is slidably and coaxially arranged within the second activator member 66, and which is releasibly connected to the holding member and to the second activator member, said drive mechanism being controlled by the first and the second activator members as will be described below. The drive mechanism is adapted to accumulate a drive force for moving the syringe carrier mechanism in a first and a second step and, after completely expelling the medicament, to force the second activator member towards the distal part of the elongated tubular housing for producing audible, visual and/or tactile feedback to a user about a completed injection.

The drive mechanism comprises a plunger rod 90 arranged to act on the stopper 92 inside said syringe 16, and a first compression spring 94 that is pre-tensioned to have an accumulated force capable of urging said plunger rod to move said syringe carrier mechanism in a first step for penetrating the needle into an injection site and to move said stopper in a second step for expelling the medicament through the needle. The plunger rod is slidably and coaxially arranged within the second activator member and the pre-tensioned first compression spring 94 is coaxially arranged within the plunger rod between a proximal end wall 98 of the plunger rod and the distal transversal end wall 76 of the second activator member. Further a guide rod 100 is arranged inside the first compression spring 94, FIG. 1*a*.

The plunger rod 90 is formed as a tube with an outer diameter somewhat smaller than the inner diameter of the syringe body to be used. The plunger rod 90 is arranged with a circumferential groove 96 having a mutual shape as that of the ledges 74 of the second activator member 66 and as that of the ledges 54 of the holding member 46 so that the annular inwardly directed ledges 74 of the second activator member 66 and the radial inwardly directed ledges 54 of the holding member 46 fit into the groove 96, FIG. 1 *b*.

The device further comprises a pre-tensioned second compression spring 102 having an annular proximal end resting on the second annular ring 64 of the first activator member 56 and an annular distal end resting on the proximal surface of stop ledges 104 of the second activator member 66, FIG. 2.

The function of the device according to the invention will now be described in connection with the FIGS. 3-6.

When the device is assembled, the distal housing part 12 is fixedly attached to proximal housing part by suitable engagement means forming the elongated tubular housing and the first and the second activator members are coaxially movable relative each other. However, when the device is in a non-activation position, the plunger is held against the accumulated force of the pre-tensioned first compression spring 94 by the inwardly directed ledges 74 of the tongues 70 of the second activator member 66 situated in the groove 96 of the plunger 90, and by the first activator member 56 which surrounds and prevents the tongues 70 from moving radially outwards. Further the ledges 54 of the holding member 46 are also arranged in the groove 96, FIG. 1 *b*. The inwardly directed ledges on the distal edge of each opening 42 of the syringe carrier 36 pass the distal end surface of the annular ledge 50 of the holding member 46 for connecting the syringe carrier to the holding member, and at the same time the tongues 34 of the needle shield 20 fit the distal surface of the ledge 60 of the first activator member 56 for connecting the needle shield to the first activator member.

The needle shield sleeve and the first activator member connected to it are arranged to be moved coaxially and distally in relation to the housing and to the second activator member against the force of the pre-tensioned second compression spring 102, when the proximal part of said needle shield sleeve is pressed against the injection site, FIG. 3. When the first activator member moves distally, the band-shaped part 72 of the second activator comes out from the surrounding of the first activator member 56, FIG. 3 and the resilient properties of the tongues 70 of the activator means allows the proximal end of the tongues 70 to flex radially outwards, causing the ledges 74 to be released from the groove 96 of the plunger rod 90. However, the ledges 54 of the holding member 46 are still in the groove 96 of the plunger rod and with the proximal end surface against the distal end of the syringe carrier 36, whereby the accumulated force from the pre-tensioned first compression spring urges said plunger rod to move in the first step said syringe carrier mechanism, whereby a penetration of the needle into the injection site is performed.

When the syringe carrier has reached its most proximal position it is forced to a stop. However the accumulated force of the pre-tensioned first compression spring acting on the plunger rod is so high that the ledges 54 of the holding member 46 are forced out of the groove of the plunger rod.

Figure 4:
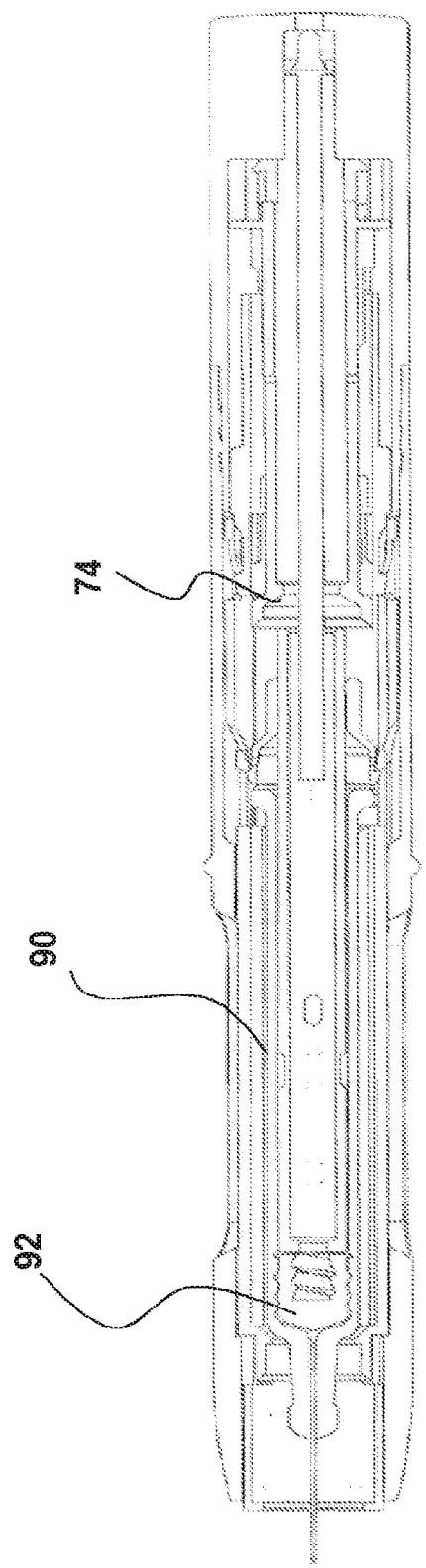

The accumulated force from the pre-tensioned first compression spring continues to urge said plunger rod to move in the second step said stopper inside the syringe and the liquid medicament is injected into the patient until the stopper reaches the inner proximal end of the syringe, FIG. 4. After the liquid medicament has been injected and the distal end of the plunger rod has passed the ledges 74 of the second activator member 66, the tongues 70 are radially moved inwards. Because the pre-tensioned first compression spring is also acting on the inner surface of the distal transversal end wall 76 of the second activator member 66 and has a remaining accumulated force, the second activator member 66 is moved distally until the outer surface of the distal transversal end wall 76 of the second activator member 66 strikes against the inner surface of the distal wall 82 of the distal housing part 12 giving an audible signal to the patient indicating that the delivery e.g. the injection has been completed and that the device can be safely removed from the injection site, FIG. 5.

Figure 5:
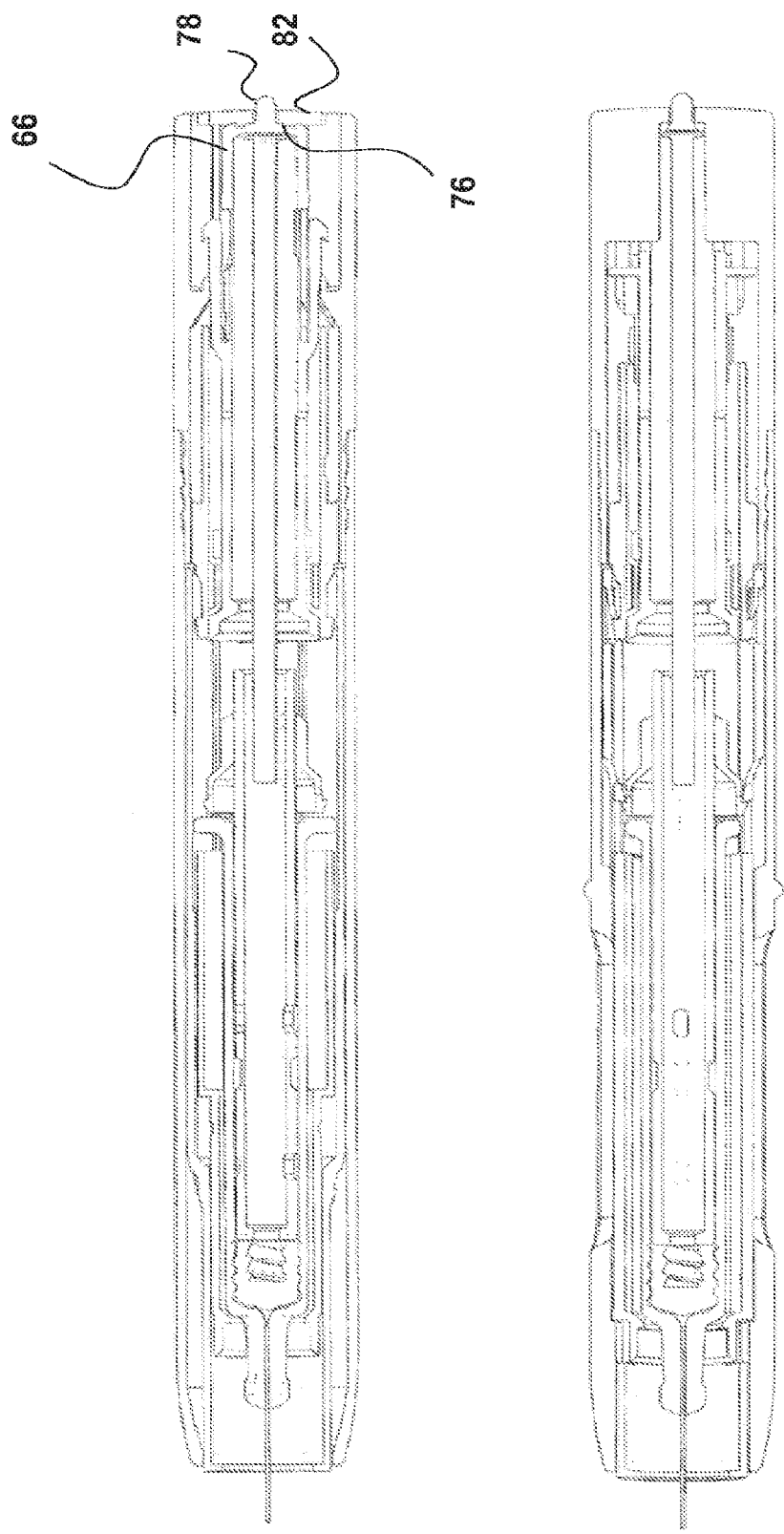

Further, the protrusion 78 of the second activator member 66 protrudes through the opening 80 becoming tactile and/or visible to provide tactile and/or visual information indicating that the injection has been completed, FIG. 5, and that the device can be safely removed from the injection site when the second activator member is coaxially and distally moved, e.g. if for instance the users finger is positioned on the end wall 82 and in addition a visual indication in that the protrusion 78 is visible through the passage 82. In order to enhance the visibility, the protrusion could be arranged with a bright colour, differing from the colour of the rest of the device.

Figure 6:
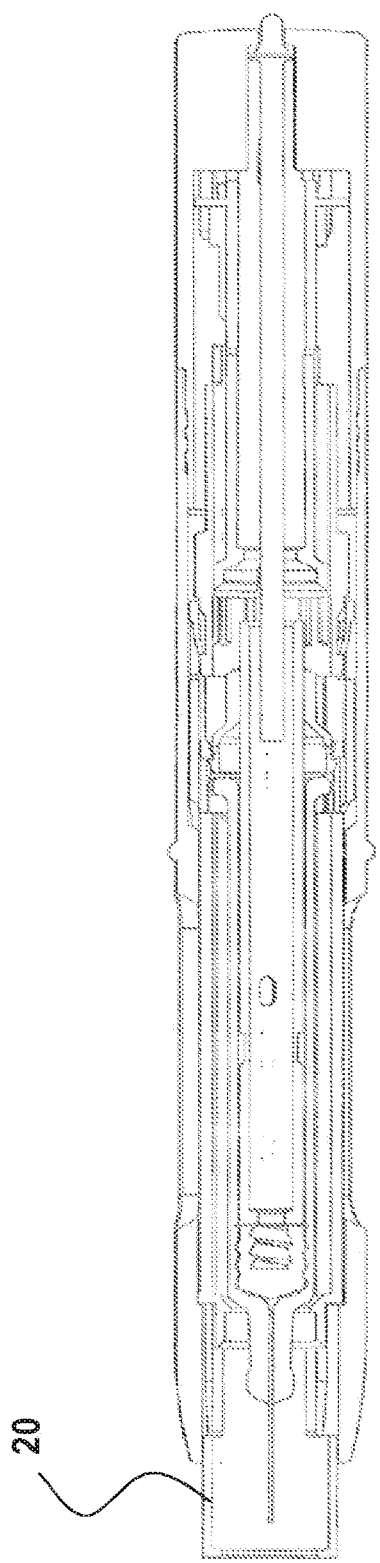

The needle shield sleeve and the first activator member are arranged to be coaxially and proximally moved in relation to the housing and to the second activator member by a force from the pre-tensioned second compression spring 102 acting on the first activator member and thus on the needle shield connected to it for covering the needle, when the proximal part of the needle shield sleeve is removed from the delivery site FIG. 6.

The first activator member 56 comprises ribs (not shown) on its inner surface arranged to interact with a band-shaped part 72 of the second activator member 66 after the needle shield sleeve and the first activator member are coaxially and proximally moved, for preventing any attempts to push the needle shield sleeve distally into the device, which prevents unintentional needle sticks.

It is to be understood that the embodiment described above and shown in the drawings is to be regarded only as a non-limiting example of the invention band that it may be modified in many ways within the scope of the patent claims.

The invention claimed is:
1. A medicament delivery device comprising:
   a generally elongated tubular housing having opposite proximal and distal parts;
   a needle shield sleeve slidably and coaxially arranged inside the housing and wherein a proximal part of said needle shield sleeve protrudes a distance outside the proximal part of the housing;
   a syringe carrier mechanism comprising a syringe carrier slidably and coaxially arranged within the needle shield sleeve, a syringe comprising a stopper, a medicament and a needle,
   wherein said syringe is coaxially arranged within said syringe carrier, and a holding member is connected to the syringe carrier;
   a first activator member slidably and coaxially arranged within the housing and connected to said needle shield sleeve;
   a second activator member slidably and coaxially arranged within the first activator member;
   a drive mechanism slidably and coaxially arranged within the second activator member and releasibly connected to the holding member and to the second activator member,
   wherein the drive mechanism comprises a plunger rod arranged to act on the stopper inside said syringe,
   wherein the plunger rod is slidably and coaxially arranged within the second activator member;
   wherein the second activator member comprises flexible tongues having annular inwardly directed ledges,
   wherein the holding member comprises flexible tongues having annular inwardly directed ledges, and
   wherein the plunger rod comprises a circumferential groove having a mutual shape as that of the ledges of the second activator member and as that of the ledges of the holding member so that the annular inwardly directed ledges of the second activator member and the radial inwardly directed ledges of the holding member fit into the groove.
2. The medicament delivery device of claim 1,
   wherein said second activator member comprises a number of longitudinally directed cut-outs being arranged along the proximal outer surface of the second activator member so as to form said flexible tongues,
   wherein the proximal end of each flexible tongue has an inclined transition surface which meets with a band-shaped part with enlarged diameter,
   wherein said annular inwardly directed ledge are arranged on the inner surface adjacent the transition surface.
3. The medicament delivery device of claim 1,
   wherein said first activator member comprises a proximal end with a conical part ending in a ledge on its outer surface,
   wherein at a distance from the ledge, a first annular ring is arranged on the outer surface, and a second annular ring is also arranged a further distance from the ledge.
4. The medicament delivery device of claim 2,
   wherein when the first activator member moves distally during use of the medicament delivery device,
   the band-shaped part of the second activator member comes out from the surrounding of the first activator member, and the resilient properties of the flexible tongues of said second activator member allows the proximal end of the tongues to flex radially outwards, causing the ledges to be released from the groove of the plunger rod.

5. The medicament delivery device of claim 2, wherein the first activator member comprises ribs on its inner surface arranged to interact with said band-shaped part of said second activator member after the needle shield sleeve and the first activator member are coaxially and proximally moved, for preventing any attempts to push the needle shield sleeve distally into the device.

6. The medicament delivery device of claim 1, wherein said drive mechanism is adapted to accumulate a drive force for moving said syringe carrier mechanism in a first step for penetrating the needle into an injection site and to move said stopper in a second step for expelling the medicament through the needle, and wherein said drive mechanism is controlled by the first and the second activator members.

7. The medicament delivery device of claim 1, wherein the drive mechanism comprises a pre-tensioned first compression spring having a force capable of urging said plunger rod to move in a first step said syringe carrier mechanism for penetrating the needle into an injection site and in a second step said stopper for expelling the medicament through the needle.

8. The medicament delivery device of claim 7, wherein the pre-tensioned first compression spring is coaxially arranged within the plunger rod between a proximal end wall of the plunger rod and the distal transversal end wall of the second activator member.

9. The medicament delivery device according to claim 8, wherein the plunger rod is arranged to be held against the force of the pre-tensioned first compression spring by the inwardly directed ledges of the tongues of the second activator member situated in the groove of the plunger rod, and by the first activator member which surrounds and prevents the tongues from moving radially outwards.

10. The medicament delivery device according to claim 9, wherein the drive mechanism further comprises a pre-tensioned second compression spring having an annular proximal end resting on a second annular ring of the first activator member and an annular distal end resting on the proximal surface of stop ledges of the second activator member.

11. The medicament delivery device according to claim 10, wherein the needle shield sleeve and the first activator member connected to it are arranged to be moved coaxially and distally in relation to the housing and to the second activator member when the proximal part of said needle shield sleeve is pressed against the injection site for allowing the inwardly directed ledges of the tongues of the second activator member to be released from the groove of the plunger rod, such that the force from the pre-tensioned first compression spring urges said plunger rod to move in a first step said syringe carrier mechanism and in a second step said stopper.

12. The medicament delivery device of claim 1, wherein said second activator member is arranged with information means arranged to cooperate with corresponding interacting means arranged on the distal part of the elongated tubular housing after the medicament is expelled such that a remaining drive force of the accumulated drive force in the drive mechanism forces the second activator member to be displaced towards the distal part of the elongated tubular housing for producing audible, visual and/or tactile feedback to a user about a completed injection.

13. The medicament delivery device of claim 1 wherein the medicament device comprises an autoinjector.

14. The medicament delivery device of claim 1 wherein the generally elongated tubular housing comprises at least one elongated opening for viewing the syringe.

15. The medicament delivery device of claim 1 wherein the proximal part of the needle shield comprises a first diameter and a distal part of the needle shield comprising a second diameter wherein the first diameter of the proximal part is different than the second diameter of the distal part.

16. The medicament delivery device of claim 1 wherein the syringe carrier comprises a tubular body having a first diameter and a proximal part of the syringe carrier comprising a neck portion comprising a second diameter, the second diameter of the neck portion different than the first diameter of the tubular body.

17. The medicament delivery device of claim 1 wherein the syringe carrier comprises at least one guide surface that cooperates with an inner surface of the needle shield in order to provide a stop mechanism against rotation of the syringe carrier in relation to the needle shield.

18. The medicament delivery device of claim 1 wherein the syringe carrier further comprises a plurality of inwardly directed flanges on an inner surface such that a space is obtained between the syringe carrier and the syringe.

19. The medicament delivery device of claim 1, further comprising a guide rod.

20. The medicament delivery device of claim 19, wherein the guide rod is arranged inside the first compression spring and is configured to guide the plunger rod.

* * * * *